US009855293B2

(12) United States Patent
Kim

(10) Patent No.: US 9,855,293 B2
(45) Date of Patent: Jan. 2, 2018

(54) NON-REDUCING END UNSATURATED MANNURONIC ACID OLIGOSACCHARIDES AND COMPOSITIONS CONTAINING SAME AS ACTIVE INGREDIENT

(71) Applicant: INDUSTRY FOUNDATION OF CHONNAM NATIONAL UNIVERSITY, Gwangju (KR)

(72) Inventor: Du Woon Kim, Gwangju (KR)

(73) Assignee: INDUSTRY FOUNDATION OF CHONNAM NATIONAL UNIVERSITY, Gwangju (KR)

( * ) Notice: Subject to any disclaimer, the term of this patent is extended or adjusted under 35 U.S.C. 154(b) by 0 days.

(21) Appl. No.: 15/069,684

(22) Filed: Mar. 14, 2016

(65) Prior Publication Data

US 2017/0065629 A1 Mar. 9, 2017

(30) Foreign Application Priority Data

Mar. 27, 2015 (KR) ........................ 10-2015-0043404

(51) Int. Cl.
*A61K 31/715* (2006.01)
*A61K 31/565* (2006.01)
*A61K 31/734* (2006.01)

(52) U.S. Cl.
CPC .......... *A61K 31/715* (2013.01); *A61K 31/565* (2013.01)

(58) Field of Classification Search
CPC ... A61K 31/715; A61K 31/734; A61K 31/565
See application file for complete search history.

(56) References Cited

U.S. PATENT DOCUMENTS 8,257,695 B2 * 9/2012 Rautonen ............. A61K 35/747 424/93.45

FOREIGN PATENT DOCUMENTS

KR 10-1277706 6/2013 ............... C12N 9/88

OTHER PUBLICATIONS

Definition of prevent, Oxford English Dictionary Online, http://dictionary.oed.com/, accessed online Mar. 27, 2010, especially definition 9a. at p. 2.*

Mayo Clinic, entry for Obesity, http://www.mayoclinic.org, accessed online on Apr. 16, 2014.*

Mayo Clinic, entry for Menopause, http://www.mayoclinic.org, accessed online on Apr. 25, 2017.*

Heyraud et al., Carbohydrate Research, 1996, 291, p. 115-126.*

Wang et al., Nutritional Research, 2006, 26, p. 597-603.*

Kim et al., Biotechnology and Bioprocess Engineering, 2011, 16, p. 843-851.*

Cani et al., Diabetologia, 2007, 50, p. 2374-2383.*

Werner et al., J. Drug Del. Sci. Tech., 2004, 14(4), p. 275-284. (Year: 2004).*

Haug, A., et al. (1966) "A study of the constitution of alginic acid by partial acid hydrolysis." ActaChemicaScandinavica, 20(1): 183-190.

Huttenhower, C., et al. (2012) "Structure, function and diversity of the healthy human microbiome." Nature 486.7402, 207-214.

Joo, D. S., et al. (1996) "Preparation of oligosaccharides from alginic acid by enzymatic hydrolysis." Korean Society of Food Science and Technology, 28(1): 146-151.

Mistuoka, T., (1982) "Recent trends in research on intestinal flora." Bifidobacteria Microflora, 1(1): 3.

Nadal, I., et al. (2009) "TS in clostridia, bacteroides and immunoglobulin-coating fecal bacteria associated with weight loss in obese adolescents." Int J Obes(Lond), 33:758-767.

Neyrinck, A.M., et al. (2011) "Prebiotic effects of wheat arabinoxylan related to the Increase in bifidobacteria, roseburia and bacteroides/prevotella in diet-induced obese mice." PLoS One,6(6) e20944.

Qin, J., et al. (2010) "A human gut microbial gene catalogue established by metagenomic sequencing." Nature, 59-65.

Turnbaugh, PJ et al. (2006) "An obesity-associated gut microbiome with increased capacity for energy harvest." Nature, 1027-31.

* cited by examiner

*Primary Examiner* — Jonathan S Lau
(74) *Attorney, Agent, or Firm* — Harness, Dickey & Pierce, P.L.C.

(57) ABSTRACT

Disclosed is a non-reducing end unsaturated mannuronic acid oligosaccharide having a molecular weight of 100-3000 Da, which is obtained by lysing polymannuronate as a substrate with alginate lyase, and provided are: a non-reducing end unsaturated mannuronic acid oligosaccharide; and pharmaceutical compositions for alleviating, preventing, or treating obesity, diabetes, and climacteric syndrome, and probiotics for promoting intestinal beneficial bacteria, the compositions and probiotics containing, as an active ingredient, the non-reducing end unsaturated mannuronic acid oligosaccharide, so that the antiobesity and antidiabetic effects, estrogen activity, and intestinal microflora controlling effect of the non-reducing end unsaturated mannuronic acid oligosaccharides are remarkably excellent as compared with non-reducing end saturated mannuronic acid oligosaccharides.

3 Claims, 14 Drawing Sheets

NON-REDUCING END UNSATURATED MANNURONIC ACID OLIGOSACCHARIDES AND COMPOSITIONS CONTAINING SAME AS ACTIVE INGREDIENT

CROSS-REFERENCE TO RELATED APPLICATIONS

This application claims the benefit and priority of Korean Patent Application No. 10-2015-0043404, filed 27 Mar. 2015. The entire disclosure of the above applications is incorporated herein by references.

FIELD

The present disclosure relates to non-reducing end unsaturated mannuronic acid oligosaccharides and compositions containing the same as an active ingredient.

BACKGROUND

In the modern world, the functional food market is expanding with the increase in complex metabolic syndromes caused by obesity (based on the year 2014, 18% of OECD adults) and diabetes (based on the year 2011, 6.9%).

The metabolic syndrome refers to the complex occurrence of obesity, type 2 diabetes caused by insulin resistance, and various metabolic abnormalities. The metabolic syndromes rapidly increase due to the aging population and high-calorie diets habits, causing social costs, and thus the prevention of fundamental causes and the development of medical or food materials are urgent.

In the human intestinal ecosystem, microbes are present at birth to maintain the balance between beneficial bacteria and harmful bacteria. The microbes form intestinal microflora, coexist with humans, and have a direct or indirect effect on human health through interactions with humans. Recently, the National Institutes of Health (NIH) researched the relationships between intestinal microflora and diseases through the "Human Microbiome Project", and raised the importance of the normalization of the intestinal flora since having unbalanced microbial flora causes the occurrence of inflammatory enteric diseases and the like.[1,2]

According to the paper about the association between obesity and gut microbiome, which was published on the scientific journal "Nature" in 2006, slim people are different from obese people with respect to gut microbiome distribution, and it was confirmed through an experiment using mice that bacteria belonging to the Firmicutes show a relatively higher component percentage than bacteria belonging to the Bacteroidetes in obese mice.[3] Since then, the research about intestinal microbes and the human body has been conducted in various fields, and the development of intestinal microflora improving preparations is needed for the suppression of obesity and the treatment of diseases through the improvement in intestinal microflora.

Approximately 500,000 species of marine organisms, which correspond to about 80% of all species on Earth, are assumed to exist. However, of these, less than 1% of the marine organisms are being developed as useful living resources, and thus have a very high development potential. Alginic acid, which is a representative seaweed polysaccharide as a seaweed-derived functional material, is contained in 15-35% of brown algae, such as kelp or seaweed, and has polyuronide characteristics, in which two kinds of uronic acids, β-D-mannuronic acid (M) and α-L-guluronic acid (G), are connected via 1,4-glycosidic linkages at various ratios. Alginic acid-derived oligosaccharides may be classified into mannuro-oligosaccharide (MOS), guluro-oligosaccharide (GOS), and mannuronate and guluronate mixed oligosaccharide (alginate oligosaccharide, AOS), according to the component sugar, and may also be classified according to the double bond at the end of sugar.

Marine-derived polysaccharides have been used in human life for a long time, and the research about biological activities, such as anticancer activity, antioxidation, antihypertension, and antibiotic materials, which are derived from marine organisms, are being conducted actively and globally. The output of alginic acid sources produced globally is approximately 100,000 tons, of which about 30% are used as a food additive, but when the alginic acid sources are developed as high value-added medicinal sources, the values thereof can be doubled. The research of alginic acid-derived oligosaccharides achieves tangible results, such as being reported to have the biological activities of promoting the growth of roots of higher plants, promoting the growth of *Bifidobacterium* sp., anti-inflammation, antioxidation, and antibiotic activity, according to the structural feature, and thus alginic acid-derived oligosaccharides have widespread application fields.

Throughout the entire specification, many papers and patent documents are referenced and their citations are represented. The disclosure of the cited papers and patent documents are entirely incorporated by reference into the present specification and the level of the technical field within which the present invention falls, and the details of the present invention are explained more clearly.

SUMMARY

The present inventors endeavored to promote the use of alginic acid oligosaccharides for food and medicine. As a result, the present inventors investigated non-reducing end unsaturated mannuronic acid oligosaccharides, which are derived from alginic acid and have various biological activities, such as antiobesity and antidiabetic actions, an improvement in intestinal microflora, and estrogen efficacy, and then completed the present invention.

Therefore, an aspect of the present disclosure is to provide non-reducing end unsaturated mannuronic acid oligosaccharides.

Another aspect of the present disclosure is to provide compositions for alleviating, preventing, or treating obesity.

Still another aspect of the present disclosure is to provide compositions for alleviating, preventing, or treating diabetes.

Another aspect of the present disclosure is to provide probiotics for promoting intestinal beneficial bacteria.

Still another aspect of the present disclosure is to provide compositions for alleviating, preventing, or treating climacteric syndrome.

Other purposes and advantages of the present disclosure will become more obvious with the following detailed description of the invention, claims, and drawings.

In accordance with an aspect of the present invention, there is provided a non-reducing end unsaturated mannuronic acid oligosaccharide having a molecular weight of 100-3000 Da, which is obtained by lysing polymannuronate as a substrate with alginate lyase.

The present inventors endeavored to promote the use of alginic acid oligosaccharides for food and medicine. As a result, the present inventors investigated non-reducing end unsaturated mannuronic acid oligosaccharides, which are derived from alginic acid and have various biological activities, such as antiobesity and antidiabetic actions, an improvement in intestinal microflora, and estrogen efficacy.

As used herein, the term "non-reducing" refers to a feature of not having carbon of an anomer (a type of diastereomer in which a hydrogen atom and a hydroxyl group attached on one carbon atom are interchanged with each other in a cyclic reaction generating hemiacetals (forming a ring between C-1 and C-5) and hemiketals (forming a ring between C-2 and C-5) of monosaccharides)) in the oligosaccharide structure.

As used herein, the term "unsaturated" refers to a form in which a carbon chain with hydrogen atoms is unsaturated, and the term "saturated" refers to a form in which a carbon chain with hydrogen atoms is saturated.

The non-reducing end unsaturated mannuronic acid oligosaccharides of the present invention include all types of mannuronic acid oligosaccharides, which have no anomeric carbon and of which a carbon chain with hydrogen atoms is unsaturated.

The non-reducing end unsaturated mannuronic acid oligosaccharide has structural formula 1 shown in an example below (a mannuronic acid oligosaccharide having three linked sugars):

[Structural Formula 1]

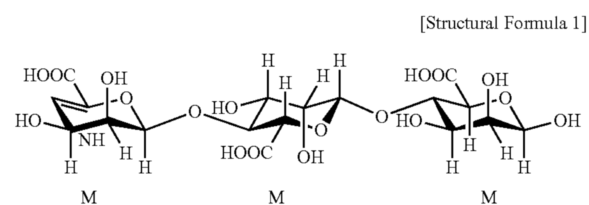

The non-reducing end unsaturated mannuronic acid oligosaccharide has a Z-average molecular weight (m/z) of 175 for one sugar, 351 for two sugars, 527.4 for four sugars, 880 for five sugars, and 1056 for six sugars, and 1232 for seven sugars (FIG. 2)

As used herein, the term "non-reducing end saturated mannuronic acid oligosaccharide" refers to a saturated mannuronic acid oligosaccharide obtained by acid hydrolysis of polymannuronate.

The non-reducing end unsaturated mannuronic acid oligosaccharide is prepared by lysing polymannuronate as a substrate with alginate lyase.

According to an embodiment of the present invention, the alginate lyase refers to an enzyme that lyses alginate, which is composed of polyguluronate and polymannuronate, into low molecules.

According to a specific embodiment of the present invention, the alginate lyase is AlyDW11 (Korean Patent Registration No. 10-1277706) derived from an abalone intestinal strain.

The non-reducing end unsaturated mannuronic acid oligosaccharide of the present invention is composed of one or more sugars.

According to an embodiment of the present invention, the non-reducing end unsaturated mannuronic acid oligosaccharide includes one to ten mannuronic acids or guluronic acids. According to another embodiment of the present invention, the non-reducing end unsaturated mannuronic acid oligosaccharide includes one to nine mannuronic acids or guluronic acids. According to still another embodiment of the present invention, the non-reducing end unsaturated mannuronic acid oligosaccharide includes one to eight mannuronic acids or guluronic acids. According to a particular embodiment of the present invention, the non-reducing end unsaturated mannuronic acid oligosaccharide includes one to seven mannuronic acids or guluronic acids.

The non-reducing end unsaturated mannuronic acid oligosaccharide of the present invention has a deletion of a water molecule, and thus has a smaller mass value by approximately 18, which corresponds to a mass value of the water molecule, compared with the non-reducing end saturated mannuronic acid oligosaccharide (FIG. 2).

The non-reducing end unsaturated mannuronic acid oligosaccharide of the present invention is composed of mannuronic acids and guluronic acids.

According to an embodiment of the present invention, the ratio of mannuronic acids:guluronic acids is 1.2-5.0:1 in the non-reducing end unsaturated mannuronic acid oligosaccharide. According to another embodiment of the present invention, the ratio is 1.2-4.5:1. According to still another embodiment of the present invention, the ratio is 1.8-4.0:1. According to a particular embodiment of the present invention, the ratio is 2.0-3.0:1.

That is, the non-reducing end unsaturated mannuronic acid oligosaccharide more predominantly contains mannuronic acids rather than guluronic acids by 1.2-5.0, 1.2-4.5, 1.8-4.0, or 2.0-3.0 times (FIG. 4).

In accordance with another aspect of the present invention, there is provided a composition for alleviating, preventing, or treating obesity, the composition containing, as an active ingredient, the non-reducing end unsaturated mannuronic acid oligosaccharide.

As used herein, the term "obesity" refers to a condition in which adipose tissues are excessively accumulated in the body so as to cause health disorders.

The non-reducing end unsaturated mannuronic acid oligosaccharide of the present invention suppresses lipid accumulation.

According to an embodiment of the present invention, the non-reducing end unsaturated mannuronic acid oligosaccharide suppresses the accumulation of triglycerides by 20-60%, 25-50%, or 30-40%, and the non-reducing end saturated mannuronic acid oligosaccharide suppresses the accumulation of triglycerides by 10-30%, 10-25%, or 10-30%.

According to another embodiment of the present invention, the non-reducing end unsaturated mannuronic acid oligosaccharide suppresses the accumulation of triglycerides by at least two times, compared with the non-reducing end saturated mannuronic acid oligosaccharide.

The non-reducing end unsaturated mannuronic acid oligosaccharide controls intestinal microflora inducing obesity.

As used herein, the term "intestinal microflora or gut microflora" refers to microorganism complex community growing in animal guts. Each microorganism constituting intestinal microflora is beneficial or harmful to hosts due to material production or lytic ability, and for example, the intestinal microflora, as a whole, is involved in providing vitamins, preventing infection and helping gut functions (peristaltic movement and absorption), and therefore, the composition of the microflora is closely related to constipation and other intestine-related diseases (Mistuoka T. Bifidobacteria Microflora, 1(1): 3, 1982).

According to an embodiment of the present invention, the non-reducing end unsaturated mannuronic acid oligosaccharide reduces the growth of intestinal bacterial strains to control the intestinal microflora.

According to another embodiment of the present invention, the intestinal bacterial strains are selected from the group consisting of *Roseburia* sp. and *Lactobacillus* sp.

The non-reducing end unsaturated mannuronic acid oligosaccharide of the present invention inhibits the expression of adipocyte differentiation-related genes inducing obesity.

According to an embodiment of the present invention, the non-reducing end unsaturated mannuronic acid oligosaccharide inhibits the expression of adipocyte protein 2 (aP2), CAAT enhancer binding protein α (C/EBPα), and peroxisome proliferator-activated receptor γ (PPARγ).

According to another embodiment of the present invention, the non-reducing end unsaturated mannuronic acid oligosaccharide inhibits the expression of aP2, C/EBPα, and PPARγ by 15-35%, 50-70%, and 30-50%, respectively. This effect is superior to that of the non-reducing end saturated mannuronic acid oligosaccharide by 1.5-7.0 times.

The composition for alleviating, preventing, or treating obesity of the present invention may be prepared as a pharmaceutical composition for preventing or treating obesity, or a food composition or functional food composition for alleviating or preventing obesity.

In accordance with still another aspect of the present invention, there is provided a composition for alleviating, preventing, or treating obesity, the composition containing, as an active ingredient, the non-reducing end unsaturated mannuronic acid oligosaccharide.

As used herein, the term "diabetes" refers to a chronic disease characterized by a relative or absolute shortage in insulin, causing glucose-intolerance. The term "diabetes" includes all types of diabetes, for example, type 1 diabetes, type 2 diabetes, or hereditary diabetes. Type 1 diabetes is the insulin-dependent diabetes, and is mainly caused by β-cell disruption. Type 2 diabetes is the insulin-independent diabetes, and is caused by an insufficient secretion of insulin after eating or by insulin resistance.

According to an embodiment of the present invention, the non-reducing end unsaturated mannuronic acid oligosaccharide promotes glucose uptake.

These effects of the present invention result from only the non-reducing end unsaturated mannuronic acid oligosaccharide, but are not exhibited by the non-reducing end saturated mannuronic acid oligosaccharide.

According to another embodiment of the present invention, the non-reducing end unsaturated mannuronic acid oligosaccharide promotes glucose uptake via the AMP-activated protein kinase (AMPK) pathway.

The composition for alleviating, preventing, or treating diabetes of the present invention may be prepared as a pharmaceutical composition for preventing or treating diabetes, or a food composition or functional food composition for alleviating or preventing diabetes.

In accordance with still another aspect of the present invention, there is provided a probiotic for promoting intestinal beneficial bacteria, containing, as an active ingredient, the non-reducing end unsaturated mannuronic acid oligosaccharide.

The probiotic for promoting intestinal beneficial bacteria of the present invention promotes the growth of intestinal beneficial bacteria.

In an embodiment of the present invention, the intestinal beneficial bacteria are selected from the group consisting of *Roseburia* sp. and *Lactobacillus* sp.

As used herein, the term "probiotic" refers to a food supplement containing living bacteria, which helps for the health of a host organic body. The probiotic composition of the present invention may be prepared as a fermented milk product, but may be prepared in the form of a granule, a powder, or the like.

The administration method of the probiotic composition of the present invention is not particularly limited, but the probiotic composition may be orally administered in the form of a pill or a tablet, or may be administered by being added to food in the form of a powder or a granule. For example, when used as a medicine, the composition of the present invention per se may be used without formulating each component powder, but may be formulated in the dosage form of a powder, a granule, a fine granule, a tablet, a sugar-coated tablet, a capsule, a tablet, an enteric-coated preparation, or the like. An excipient, a binder, a disintegrant, or the like, which is used in general medicinal preparations, may be used as a diluent, and besides, a colorant, a stabilizer, a preserver, a lubricant, or the like may be added. When used as food, the food composition of the present invention per se may be used without formulating each component powder, but may be processed in a form that is suitable to uptake by adding a plant fiber, an oligosaccharide, a grain, a vitamin, and the like, or adding a flavoring, a colorant, a sweetening agent, and the like. In addition, the food composition, as a food additive, may be added and mixed with another food.

The probiotic for promoting intestinal beneficial bacteria of the present invention may be prepared into a pharmaceutical composition, a food composition, or a functional food composition.

In accordance with another aspect of the present invention, there is provided a composition for alleviating, preventing, or treating climacteric syndrome, the composition containing, as an active ingredient, the non-reducing end unsaturated mannuronic acid oligosaccharide.

As used herein, the term "climacteric syndrome" is a kind of female internal secretion syndrome, and refers to a transition period of the reduction or loss of physiological and sexual functions through general and gradual reductions of ovarian functions regardless of natural loss, loss of surgery, or chemically induced loss, and reaching the menopause, as one procedure during the climacteric period, which is a permanent stop of menstruation occurring after the ovarian functions are stopped. In the menopausal period, acute or chronic symptoms may occur depending on hormone changes, such as the reduction in estrogen production, the increases in follicle stimulating hormone and luteinizing hormone, etc. That is, vasomotor symptoms, such as hot flushes and night sweating, and psychological symptoms, such as anxiety, lack of concentration, and depression, may be shown as initial symptoms, and there may be urinary reproductive system and skin symptoms within a few years of menopause, and there may be osteoporosis, cardiovascular, and cerebrovascular diseases in few years after menopause.

The climacteric syndromes include a symptom selected from the group consisting of facial flushing, sweating, heart discomfort, sleep problems, depression, irritability, anxiety, physical fatigue, mental fatigue, sexual problems, urinary problems, vaginal dryness, joint discomfort, and muscle discomfort.

The composition containing the non-reducing end unsaturated mannuronic acid oligosaccharide as an active ingredient of the present invention increases the activity of estrogen.

The non-reducing end unsaturated mannuronic acid oligosaccharide activates estrogen through the expression of estrogen response element (ERE)-mediated underlying genes via an estrogen receptor pathway, in which estrogen acts as a ligand, and an estrogen-related receptor α pathway, which acts independently from estrogen.

According to an embodiment of the present invention, the non-reducing end unsaturated mannuronic acid oligosaccharide induces the expression of ERE via estrogen receptor α.

According to another embodiment of the present invention, the non-reducing end unsaturated mannuronic acid oligosaccharide induces the expression of ERE by expressing estrogen-related receptor α.

The activity of estrogen is increased through the expression of underlying estrogen genes due to the expression of ERE.

According to still another embodiment of the present invention, the non-reducing end unsaturated mannuronic acid oligosaccharide increases the mRNA expression of presenilin 2 (pS2), progesterone receptor (PR), and E2-mediated cathepsin D (CTSD).

According to another embodiment of the present invention, the non-reducing end unsaturated mannuronic acid oligosaccharide increases the mRNA expression of peroxisome proliferator-activated receptor gamma coactivator 1-α (PGC-1α), estrogen-related receptor α (ERRα), trans-acting T-cell-specific transcription factor (GATA3), and forkhead box protein A1 (FOXA1).

GATA3 and FOXA1 are important factors in mammary cell differentiation, and serve to inhibit the differentiation into cancer cells or malignant tumors.

The composition of the present invention further contains 17β-estradiol.

According to an embodiment of the present invention, the non-reducing end unsaturated mannuronic acid oligosaccharide shows a synergic effect together with 17β-estradiol.

The composition of the present invention may be prepared as a pharmaceutical composition for preventing or treating climacteric syndrome, or a food composition or functional food composition for alleviating or preventing climacteric syndrome.

Here, (a) the composition for alleviating, preventing, or treating obesity; (b) the composition for alleviating, preventing, or treating diabetes; (c) the probiotic for promoting intestinal beneficial bacteria; and (d) the composition for alleviating, preventing, or treating climacteric syndrome, of the present invention, may be prepared into a pharmaceutical composition.

According to a preferable embodiment of the present invention, the composition of the present invention contains: (a) a pharmaceutically effective amount of the above-described non-reducing end unsaturated mannuronic acid oligosaccharide of the present invention; and (b) a pharmaceutically acceptable carrier. As used herein, the term "pharmaceutically effective amount" refers to an amount that is sufficient to attain the efficacy or activity of the above-described non-reducing end unsaturated mannuronic acid oligosaccharide.

In cases where the composition of the present invention is prepared as a pharmaceutical composition, the pharmaceutical composition of the present invention contains a pharmaceutically acceptable carrier. The pharmaceutically acceptable carrier contained in the pharmaceutical composition of the present invention is conventionally used at the time of formulation, and examples thereof may include, but are not limited to, lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, and mineral oil. The pharmaceutical composition of the present invention may further contain a lubricant, a wetting agent, a sweetening agent, a flavoring agent, an emulsifier, a suspending agent, a preservative, and the like, in addition to the above ingredients. Suitable pharmaceutically acceptable carriers and preparations are described in detail in *Remington's Pharmaceutical Sciences* (19th ed., 1995).

The pharmaceutical composition of the present invention may be administered orally or parenterally, and preferably, the oral administration manner is employed.

A suitable dose of the pharmaceutical composition of the present invention may vary depending on various factors, such as the method for formulation, manner of administration, the age, body weight, gender, and morbidity of the patient, diet, time of administration, excretion rate, and response sensitivity. A general dose of the pharmaceutical composition of the present invention is within the range of 0.001 μg/kg-100 mg/kg in adults.

The pharmaceutical composition of the present invention may be formulated into a unit or multiple dosages form using a pharmaceutically acceptable carrier and/or excipient according to the method easily conducted by a person having an ordinary skill in the art to which the present invention pertains. Here, the dosage form may be a solution in an oily or aqueous medium, a suspension, a syrup, or an emulsion, an extract, a powder, a granule, a tablet, or a capsule, and may further include a dispersant or a stabilizer.

As used herein, the term "containing, as an active ingredient" refers to the inclusion of an amount that is sufficient to attain the efficacy or activity of the above-described non-reducing end unsaturated mannuronic acid oligosaccharide. The quantitative upper limit of the above-described non-reducing end unsaturated mannuronic acid oligosaccharide contained in the composition of the present invention may be selected within an appropriate range by a person skilled in the art.

Here, (a) the composition for alleviating, preventing, or treating obesity; (b) the composition for alleviating, preventing, or treating diabetes; (c) the probiotic for promoting beneficial bacteria; and (d) the composition for alleviating, preventing, or treating climacteric syndromes, of the present invention, may be prepared into a food composition.

In cases where the composition containing, as an active ingredient, the non-reducing end unsaturated mannuronic acid oligosaccharide of the present invention, is prepared into a food composition, it contains components that are generally added at the time of food making, besides the non-reducing end unsaturated mannuronic acid oligosaccharide, and contains, for example, proteins, hydrocarbons, fats, nutrients, seasonings, and flavoring agents. Examples of the carbohydrate are monosaccharides, such as glucose and fructose; disaccharides, such as maltose, sucrose, and oligosaccharides; polysaccharides such as dextrin; typical sugars such as cyclodextrin; sugar alcohols, such as, xylitol, sorbitol, and erythritol. Examples of the flavoring agent may be natural flavoring agents (thaumatin, and stevia extract (e.g., rebaudioside A, glycyrrhizin, etc.)) and synthetic flavoring agents (saccharin, aspartame, etc.) For example, a drink, which is made from the food composition, may further contain citric acid, liquefied fructose, sugar, glucose, acetic acid, malic acid, fruit juice, an extract of *Eucommia ulmoides*, a jujube extract, and an licorice extract, in addition to the non-reducing end unsaturated mannuronic acid oligosaccharide of the present invention.

The composition of the present invention may be prepared as a functional food composition containing, as an active ingredient, the non-reducing end unsaturated mannuronic acid oligosaccharide of the present invention. The composition of the present invention, when prepared as a functional food composition, contains components that are normally added at the time of food making, for example, proteins, carbohydrates, fats, nutrients, seasoning, and flavoring agents. For example, the composition of the present invention, when used as a drink, may contain a flavoring agent or a natural hydrocarbon as an additive component, in addition to the non-reducing end unsaturated mannuronic acid oligosaccharide. Examples of the natural hydrocarbon include monosaccharides (e.g., glucose, fructose, etc.); disaccharides (e.g., maltose, sucrose, etc.); oligosaccharides; polysaccharides (e.g., dextrin, cyclodextrin, etc.); and sugar alcohols (e.g., xylitol, sorbitol, erythritol, etc.). As the flavoring agent, natural flavoring agents (e.g., thaumatin, stevia extract etc.) and synthetic flavoring agents (e.g., saccharin, aspartame, etc.,) may be used.

The non-reducing end unsaturated mannuronic acid oligosaccharide is an active ingredient for biological activity of alginate, which is known in the prior art, and exhibits an antiobesity effect, an antidiabetic effect, an effect of improving climacteric syndrome, and an effect of controlling intestinal microflora. These effects are remarkably superior compared with the non-reducing end saturated mannuronic acid oligosaccharide, and this means that the double bond at the end sugar of the non-reducing end saturated mannuronic acid oligosaccharide and the unsaturated form thereof are important factors.

Features and advantages of the present invention are summarized as follows:

(a) The present invention provides non-reducing end unsaturated mannuronic acid oligosaccharides, and pharmaceutical compositions for alleviating, preventing, or treating obesity, diabetes, and climacteric syndrome, and probiotics for promoting intestinal beneficial bacteria, the pharmaceutical compositions and the probiotics contain the non-reducing end unsaturated mannuronic acid oligosaccharide as an active ingredient.

(b) The present invention leads to a production of non-reducing end unsaturated mannuronic acid oligosaccharides, which are active materials of alginate, and thus provides its excellent antiobesity effect, antidiabetic effect, estrogen activity, and an intestinal microflora controlling effect.

(c) These effects are remarkably excellent compared with mannuronic acid oligosaccharides having a non-reducing end saturated mannuronic acid oligosaccharide of the prior art.

BRIEF DESCRIPTION OF THE DRAWINGS

The above and other objects, features, and advantages of the present invention will be more apparent from the following detailed description taken in conjunction with the accompanying drawings, in which.

DETAILED DESCRIPTION

Figure 1:
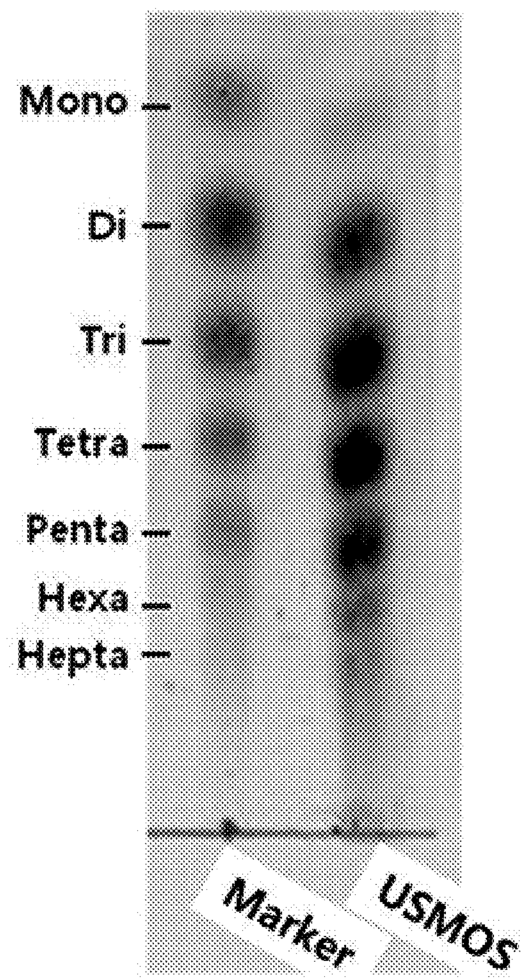
FIG. 1 shows thin-layer chromatography results of non-reducing end unsaturated mannuronic acid oligosaccharides.

Hereinafter, embodiments of the present invention will be described below in detail with reference to the accompanying drawings, so that those of ordinary skill in the art may easily work the embodiments. However, the present invention may be realized in various different forms, and therefore is not limited to embodiments to be described herein.

Example 1: Preparation of Alginic Acid Oligosaccharide

For the preparation of poly-mannuronate (poly M), 1 g of sodium alginate (Wako, Osaka Japan) and 100 ml of 0.3 M HCl were placed together, and heated at 100° C. for 2 hours. The heated sodium alginate-HCl solution was centrifuged at 500 g for 5 min, and the separated precipitate was dissolved in distilled water. After NaCl was added such that the precipitate dissolved in the distilled water has 0.1 M, the solution was adjusted to pH of 2.8-3.0, and then centrifuged at 500 g for 5 min to separate supernatant and precipitate. The separated precipitate and supernatant were subjected to alcohol precipitation and drying, to prepare poly M from the supernatant and poly G from the precipitate, which were used as substrates for preparing mannuronic acid oligosaccharides using alginate lyase (Haug, A et al. A study of the constitution of alginic acid by partial acid hydrolysis. *ActaChemicaScandinavica,* 1966, 20(1): 183-190, and Joo, D. S. et al. Preparation of oligosaccharides from alginic acid by enzymatic hydrolysis. *Korean Society of Food Science and Technology,* 1996, 28(1): 146-151).

For the preparation of non-reducing end unsaturated mannuronic acid oligosaccharides, a transgenic strain was used, wherein the transgenic strain was produced by recombining a gene corresponding to ORF11, which was selected from metagenomic library of intestine DNA of abalone inhabiting the sea near Yeosu, Korea in February 2009, and has an excellent mannuronic acid lysing ability, in pMAL-c2× expression vector, and then cloning it in the BL21(DE3) strain (Korean Patent No 10-1277706).

500 ml of the transgenic strain was inoculated in Luria-Bertani (LB) supplemented with 40 L of ampicillin (100 μg/ml), and cultured at 37° C. When the absorbance at 600 nm reached 0.4-0.5, isopropyl-β-D-thiogalactopyranoside (IPTG) was added to the culture to a final concentration of 0.3 mM, followed by culturing for 12 hours. On the completion of the culturing, the culture was centrifuged at 9,000 g for 15 min to precipitate cells. After the precipitated cells were suspended in 10 mM phosphate buffer (pH 7.0), sonication was performed for cell membrane disruption, and centrifugation at 9,000 g for 15 min was performed for coenzyme isolation. After the centrifugation, the separated supernatant was used as a coenzyme. 0.3% poly-mannuronate (poly M) was dissolved in 1 L of 10 mM phosphate buffer (pH 7.0), and $AgNO_3$ was added to a final concentration of 1 mM. A substrate lysis reaction was conducted at 45° C. for 48 h using a 2.5 L-fermentor (KBT KB-250, Japan). After the reaction, the resultant material was filtered through an ultrafiltration membrane system (Vivaflow 50, Sartorius, Ag, Germany) to obtain a mixture of oligosaccharides with a molecular weight of 3,000 Da or less, followed by lyophilization, to prepare non-reducing end unsaturated mannuronic acid oligosaccharides.

Thin-layer chromatography was performed to investigate the production of oligosaccharides, and the method thereof was as follows. The non-reducing end unsaturated mannuronic acid oligosaccharides were dissolved in water to a concentration of 0.1 mg/μl, and then 3 μl of the solution was spotted on silica gel plate (Merck KGaA, Germany). The non-reducing end unsaturated mannuronic acid oligosaccharides were sorted by the size thereof using a development solvent (1-butanol:formic acid:water=4:6:1), and then the presence of oligosaccharides was confirmed using a color developing reagent (anise aldehyde 0.5 ml, acetic acid 10 ml, MeOH 85 ml, $H_2SO_4$ 5 ml) added with sulfuric acid.

Example 2: Composition and Structural Characterization of Non-Reducing End Unsaturated Mannuronic Acid Oligosaccharides In the present example, poly mannuronate was lysed with AlyDW11 alginate lyase to secure a mixture of the non-reducing end unsaturated mannuronic acid oligosaccharides, from which fractions with a molecular weight of 3000 Da or less were then secured using an ultrafiltration membrane system (VivaFlow 50, Sartorius). In order to analyze component sugars of the non-reducing end unsaturated mannuronic acid oligosaccharides, the prepared sample was purified using an ion exchange resin column (Hitrap DEAE Sepharose FF, GE Healthcare), followed by lyophilization. The purified non-reducing end unsaturated mannuronic acid oligosaccharides were dissolved in water, and then the solution was injected into UPLC/MS system to analyze component sugars thereof.

For setting ultra performance liquid chromatography (UPLC, Waters), ACQUITY UPLC BEH C18 column (1.7 μm 1.0×100 mm, Waters) was used, and the linear gradient of solvent A (15 mM amylamine and 25 mM hexafluoroisopropanol (HFIP)) and solvent B (15 mM amylamine and 25 mM HFIP in acetonitrile) was controlled at 0.4 ml/min for 12 min. The eluate separated from $C_{18}$-UPLC was analyzed using a mass spectrometer (Quadrupole-Time of Flight, Q-TOF, Waters). Q-TOF analysis was carried out in the ESI negative mode, and the conditions were: capillary and cone voltages were 3 kV and 40 V, respectively; desolvation flow rate was 600 L/h; temperature was 300° C.; and source temperature was 120° C. TOF MS data was analyzed at a scan time of 0.5 s in the range m/z 100-1300. For accurate analysis, 2 ng/μl leucine enkephalin (554.2619 Da in ESI negative mode) was used as a lock spray for all analysis.

Figure 2:
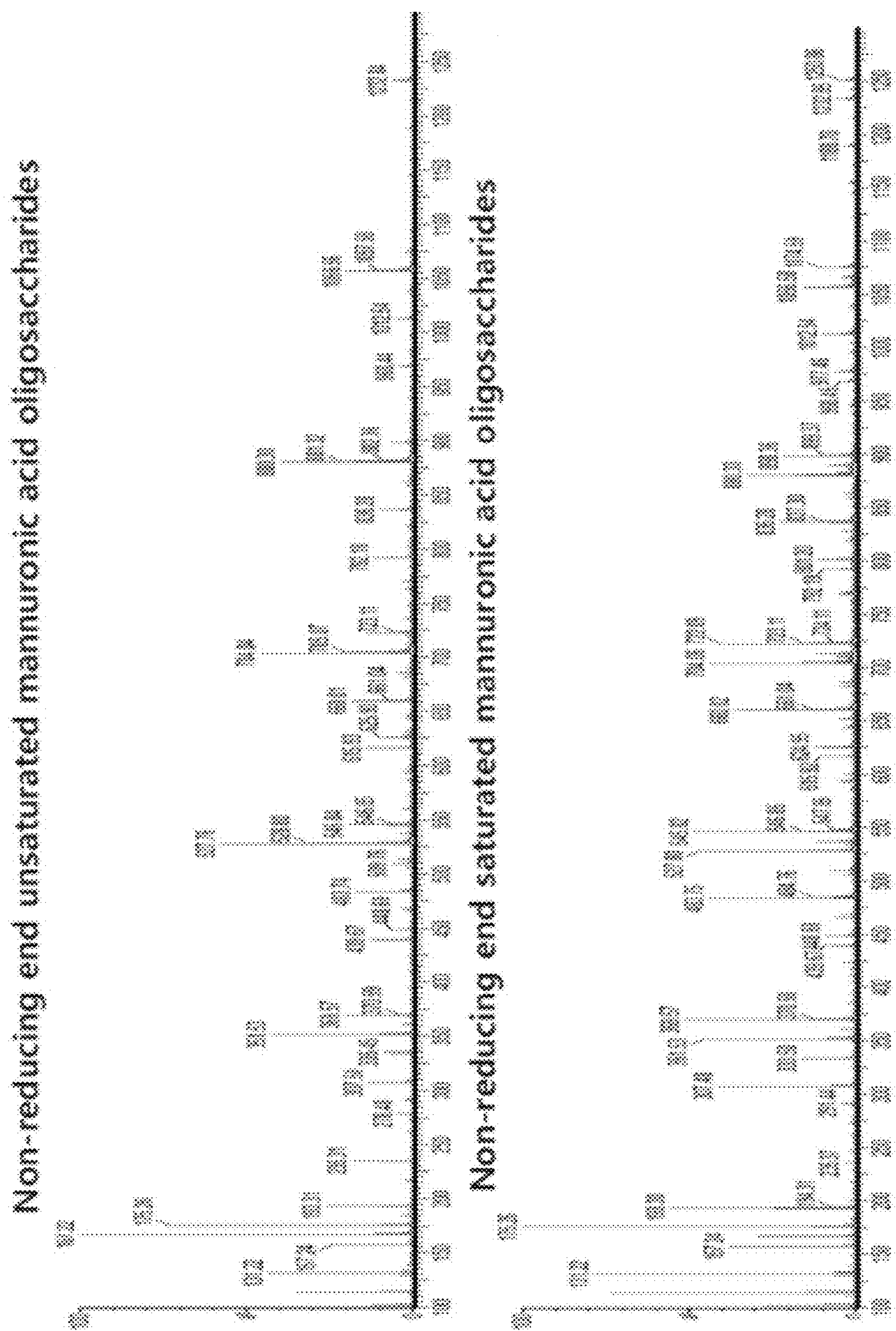
FIG. 2 shows mass analysis results of non-reducing end unsaturated mannuronic acid oligosaccharides and non-reducing end saturated mannuronic acid oligosaccharides.

As can be seen in FIG. 2, as a result of mass analysis results of the non-reducing end unsaturated mannuronic acid oligosaccharides, the non-reducing end unsaturated mannuronic acid oligosaccharides are composed of one to seven sugars, and especially, peaks having mass values, which are smaller than the previously reported mass values of mannuronic acid oligosaccharides by 18, were observed, and thus it can be seen that non-reducing end saturated mannuronic acid oligosaccharides are formed through the removal of a water molecule, and are more dominant than non-reducing end saturated mannuronic acid oligosaccharides (SMOS).

Figure 3:
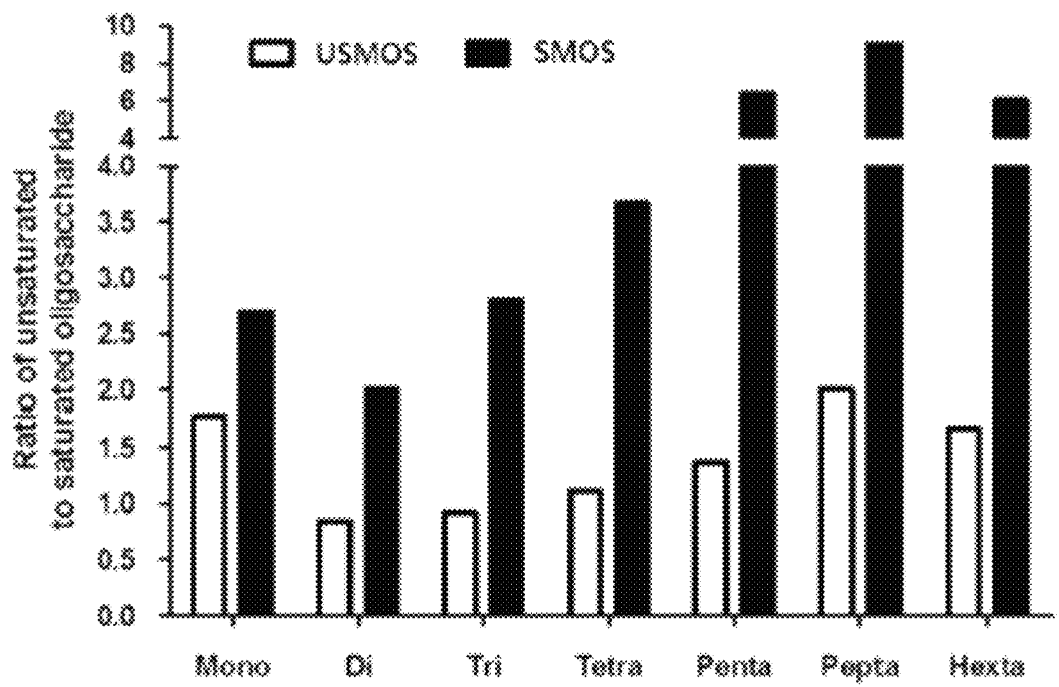
FIG. 3 shows a double bond ratio of non-reducing end unsaturated mannuronic acid oligosaccharide (USMOS) and non-reducing end saturated mannuronic acid oligosaccharide (SMOS)

The results showing the ratios of non-reducing end unsaturated mannuronic acid oligosaccharide (USMOS) to non-reducing end saturated mannuronic acid oligosaccharide (SMOS) were present in FIG. 3. As shown in FIG. 3, it was verified that the non-reducing end unsaturated mannuronic acid oligosaccharides had, on average, two times or more monosaccharides than the non-reducing end saturated mannuronic acid oligosaccahrides. The molecular weights of the non-reducing end saturated mannuronic acid oligosaccharides are as follows: 1 sugar (m/z 193), 2 sugars (m/z 369), 3 sugars (m/z 545), 4 sugars (m/z 722), 5 sugars (m/z 898) 6 sugars (m/z 1074), 7 sugars (m/z 1250).

In order to measure the percentage of mannuronic acids in the non-reducing end unsaturated mannuronic acid oligosaccharides, a circular dichroism (CD) spectroscopy signal was measured using circular dichroism spectroscopy (CD, J-715 spectropolarimeter, JASCO). CD signals were measured in the region of 190-250 nm using a cuvette (1 cm) at room temperature, and in order to obtain consistent CD signals, the non-reducing end unsaturated mannuronic acid oligosaccharides were used at 1 mg/ml. In order to investigate the composition ratio of mannuronic acid:guluronic acid, the ratio of mannuronic acid and guluronic acid was calculated by measuring a peak (an absorbance value at 200 nm) and a trough (an absorbance value at 215 nm). The calculation is as follows:

peak/trough<1, mannuronic acid/guluronic acid=2.0 (peak/trough) (1)

peak/trough>1, mannuronic acid/guluronic acid=27 (peak/trough)+40 (2)

Figure 4:
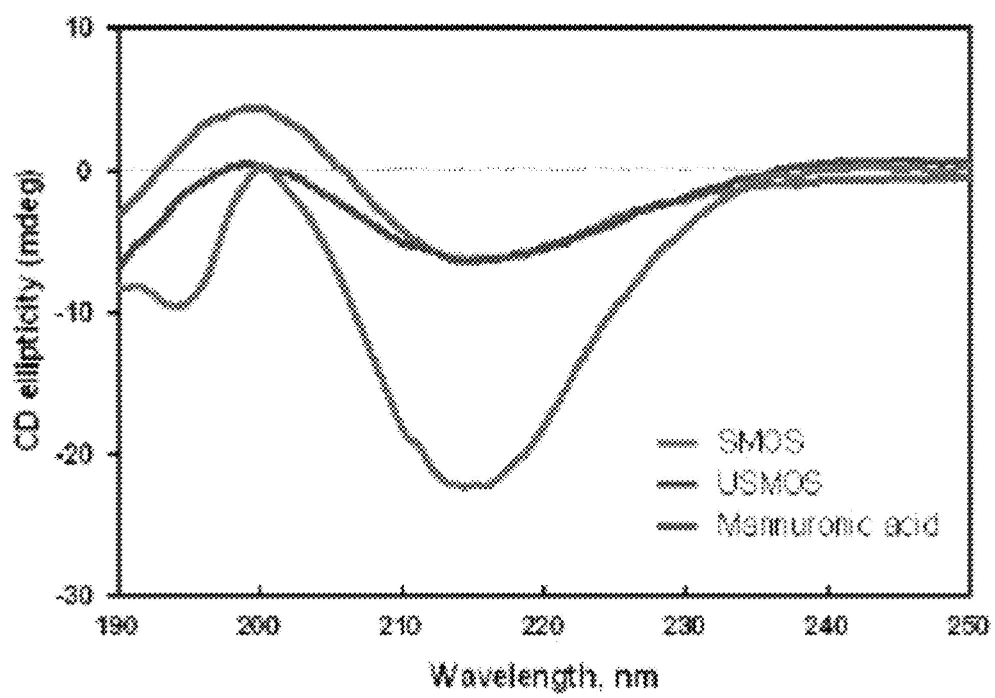
FIG. 4 shows circular dichroism (CD) confirmation results of the sugar composition of non-reducing end unsaturated mannuronic acid oligosaccharide (USMOS) and non-reducing end saturated mannuronic acid oligosaccharide (SMOS)

As can be seen from FIG. 4, it was confirmed that the non-reducing end unsaturated mannuronic acid oligosaccharides had a mannuronic acid/guluronic acid ratio of 2.12 (peak=6.66, trough=6.42).

Example 3: Suppression of Non-Reducing End Unsaturated Mannuronic Acid Oligosaccharides On Adipocyte Lipid Accumulation When 3T3-L1 preadiocytes were cultured in DMEM medium to reach confluence, the cells were treated with 0.5 mM isobutylmethylxanthine (IBMX), 1 mM dexamethasone, and 1 μg/ml insulin (MDI) for 2 days, and then the medium was exchanged with DMEM+serum medium supplemented with 1 μg/ml insulin at an interval of 48 hours, to induce the differentiation into adipocytes for 7 days. At the time of the exchange of medium, the cells were treated with the non-reducing end unsaturated mannuronic acid oligosaccharides at 0.2 mg/ml. After 7 days, the adipocyte lipid accumulation and the degree of suppression of differentiation were observed by Oil red O staining and RNA extraction, and the results were depicted in FIG. 5*a*.

Figure 5A:
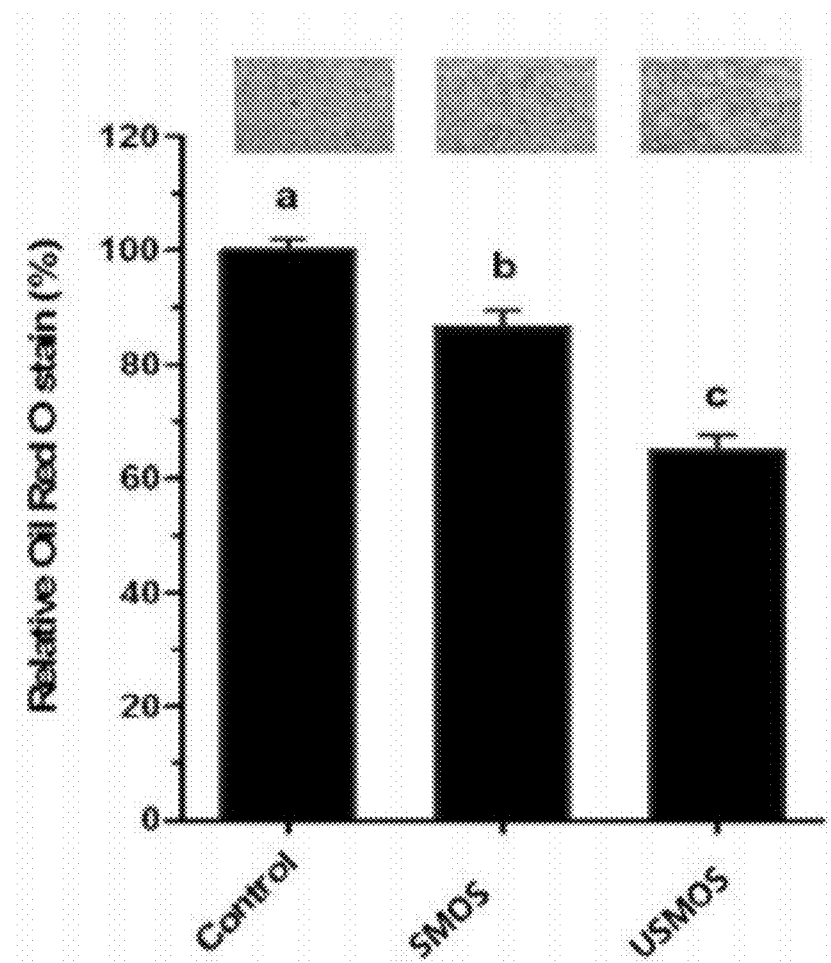
FIGS. 5*a* and 5*b* show results of inhibiting lipid accumulation and inhibiting the expression of obesity-related genes aP2, C/EBPα, and PPARγ using real-time PCR, by the treatment with non-reducing end unsaturated mannuronic acid oligosaccharide (USMOS)

As can be seen from FIG. 5*a*, as a result of observing triglycerides, which were stained with Oil red O, using an optical microscope, the treatment with non-reducing end unsaturated mannuronic acid oligosaccharides at 0.2 mg/ml resulted in a significantly weaker Oil red O staining intensity in the adipocytes, compared with a control. Further, as a quantitative result of triglycerides, which were stained with Oil red O, through pigment extraction, USMOS having a double bond at the non-reducing end suppressed triglyceride accumulation by about 40%, compared with the control, and non-reducing end saturated mannuronic acid oligosaccharides suppressed the lipid accumulation by about 15%, compared with the control. Hence, it was verified that the formation of a double bond is an important factor in the antiobesity effect.

3T3-L1 preadiocytes were differentiated into adipocytes by the same method. The cells were treated with non-reducing end unsaturated mannuronic acid oligosaccharides at 0.2 mg/ml, and then RNA extraction was conducted by the GeneJET RNA purification kit, and thereafter, the results of the inhibition of the expression of aP2, adipose differentiation-related gene CAAT enhancer binding protein α (C/EBPα), and peroxisome proliferator-activated receptor γ (PPARγ), which are adipose differentiation markers, were depicted in FIG. 5*b*.

Figure 5B:
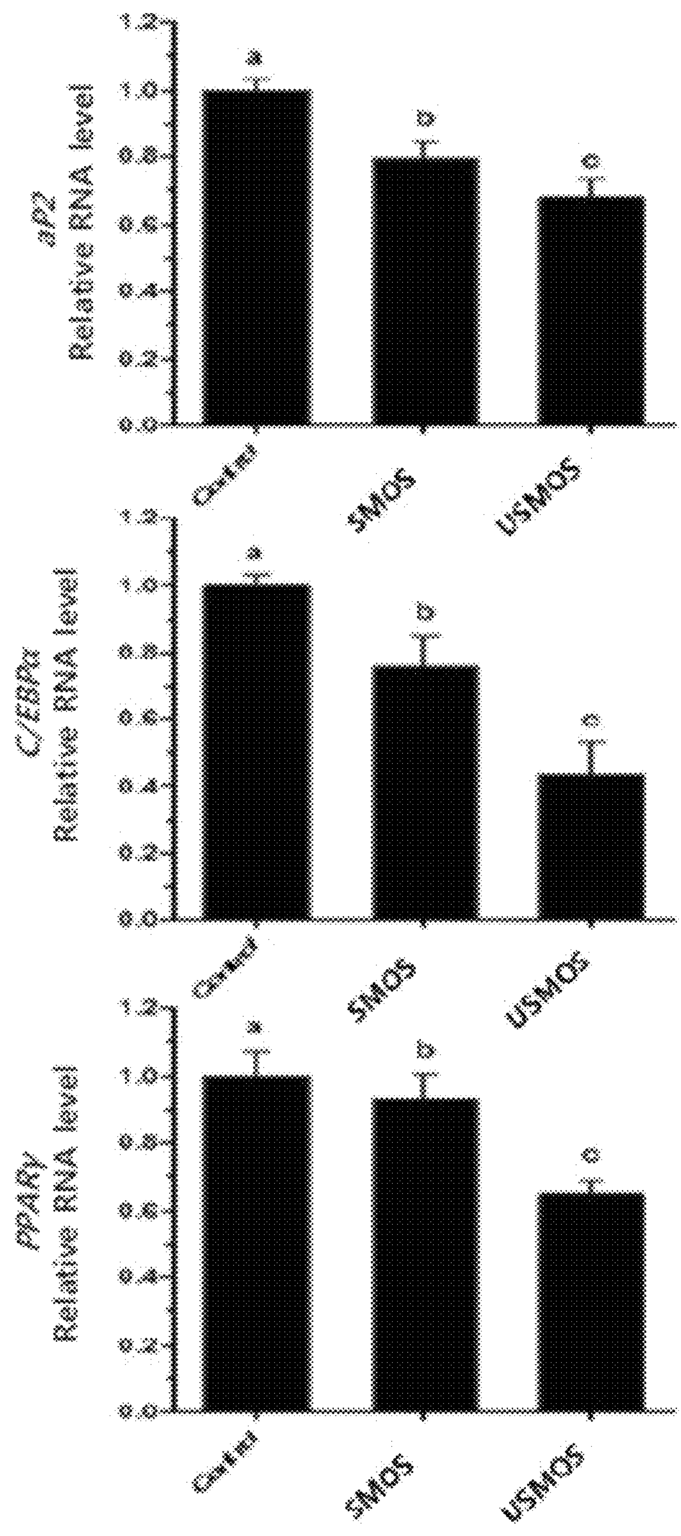

As shown in FIG. 5*b*, it was verified that the treatment with non-reducing end unsaturated mannuronic acid oligosaccharides reduced the expression levels of aP2, C/EBPα, and PPARγ by 25%, 60%, and 40%, respectively, compared with the control. In addition, it was verified that the non-reducing end unsaturated mannuronic acid oligosaccharides had an excellent antiobesity effect, compared with the non-reducing end saturated mannuronic acid oligosaccharides.

Example 4: Verification on Control of Glucose Uptake by Non-Reducing End Unsaturated Mannuronic Acid Oligosaccharides L6 muscle cells were cultured in DMEM medium containing 10% serum, and the L6 cells were completely differentiated while the medium was exchanged with 2% serum medium. The culture medium containing the completely differentiated L6 muscle cells was exchanged with serum-free DMEM medium, and the cells were treated with non-reducing end unsaturated mannuronic acid oligosaccharides at 0.2 mg/ml for 1 hour. After that, the medium treated with non-reducing end unsaturated mannuronic acid oligosaccharides was discarded, followed by washing two times with previously warmed Krebs-Ringer Hepes buffer (KRH buffer) at 37° C., thereby removing glucose in the medium. After the treatment with 0.04 mM [$^3$H]-2-deoxyglucose for 15 min, the KRH buffer, which contained [$^3$H]-2-deoxyglucose, was promptly discarded, and then ice-cooled PBS was added to stop the reaction. The cells were disrupted using a cell lysis buffer, and then the radioactivity measurement was conducted using a scintillation counter to investigate a glucose transport ability increasing effect by alginic acid oligosaccharide treatment.

Figure 6A:
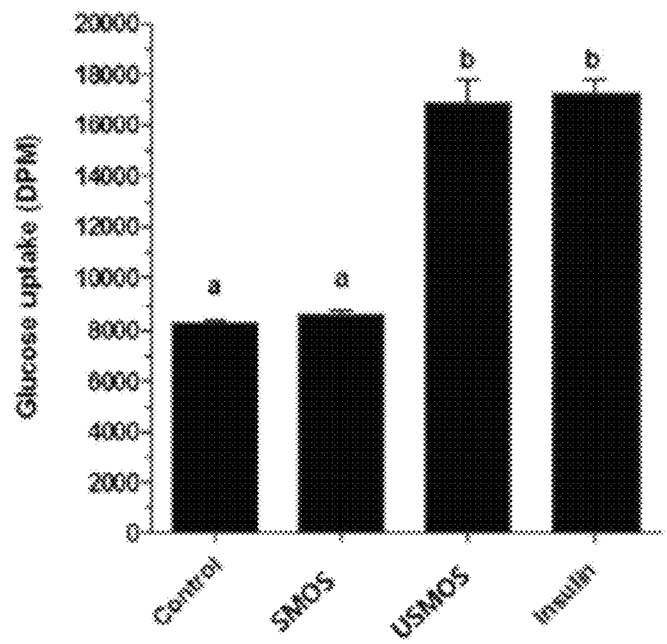
FIGS. 6*a* to 6*c* show glucose uptake promotion results and expression levels of related proteins, p-PAK, p-Akt, and p-AS160, by the treatment with non-reducing end unsaturated mannuronic acid oligosaccharide (USMOS)
Figure 6B:
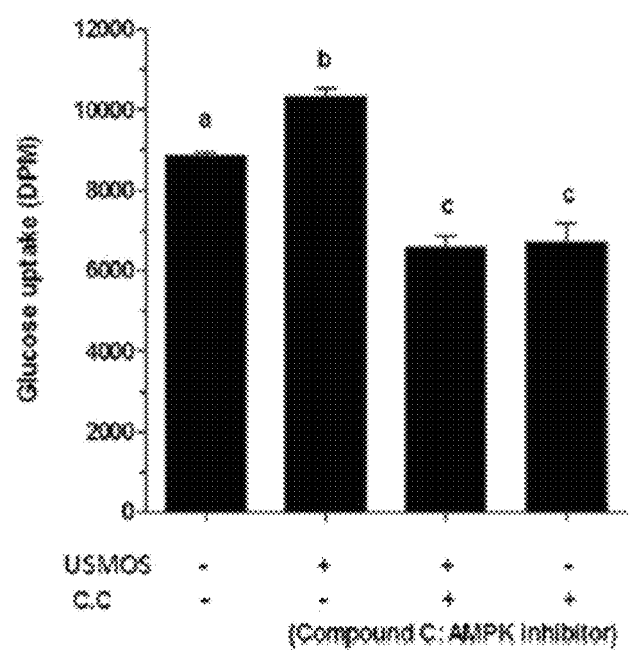

As shown in FIG. 6*a*, it was verified that the treatment with non-reducing end unsaturated mannuronic acid oligosaccharides promoted the intracellular glucose uptake to a similar degree, compared with insulin (0.2 μM) as a positive control. It was verified that, as the treatment with non-reducing saturated mannuronic acid saccharide at 0.2 mg/ml did not lead to glucose uptake, the formation of a double bond at the non-reducing end was important in the promotion of glucose uptake. In addition, it was verified that, as the co-treatment with non-reducing end unsaturated mannuronic acid oligosaccharides and 1 μM compound C (C. C), which is an inhibitor of AMP-activated protein kinase (AMPK) as an important protein in glucose uptake, suppressed glucose uptake, the non-reducing end unsaturated mannuronic acid oligosaccharides promoted the glucose uptake via AMPK pathway (FIG. 6*b*).

Figure 6C:
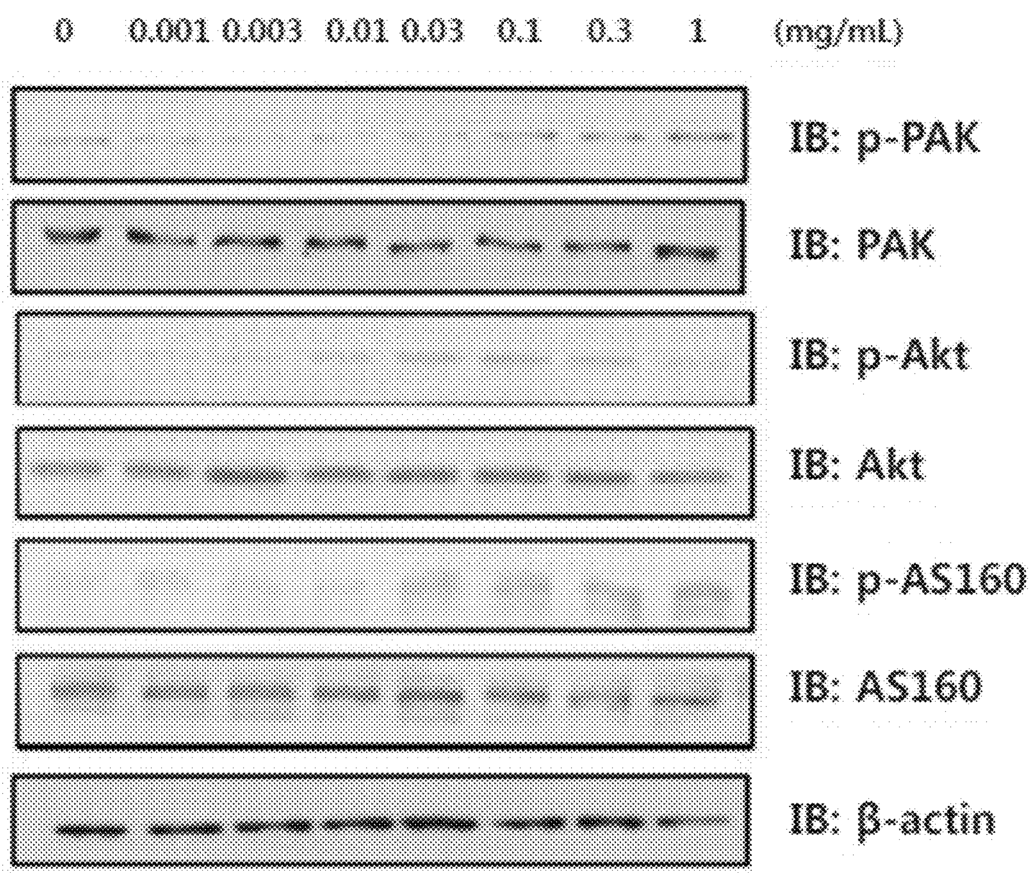

In order to investigate an increase in phosphorylation of PAK, Akt, and AS160, which influence the expression of transporters related to the promotion of glucose uptake, by the treatment with non-reducing end unsaturated mannuronic acid oligosaccharides, the muscle cells were treated with different concentrations of non-reducing end unsaturated mannuronic acid oligosaccharides, followed by protein extraction and western blotting. As a result, as shown in FIG. 6*c*, it was verified that the phosphorylation was increased in a dose-dependent manner of the non-reducing end unsaturated mannuronic acid oligosaccharides. Therefore, it was anticipated that the non-reducing unsaturated mannuronic acid oligosaccharides would promote the AMPK pathway and the phosphorylation of PAK, Akt, and AS160, for the promotion of glucose uptake, to influence the expression of glucose transporter 4 (GLUT4).

Example 5: Verification on Intestinal Microflora Controlling Efficacy by Non-Reducing End Unsaturated Mannuronic Acid Oligosaccharides In order to investigate the intestinal microflora improvement efficacy of non-reducing end unsaturated mannuronic acid oligosaccharides, rats were used as obese animal models and mice were used as aged animal models. 3-week aged male SD rats, as obesity-induced rats, were purchased from Central Lab. Animal Inc, and then acclimatized for 3 days. The feeding environment was as follows: temperature was 20±2° C., relative humidity was 50±10%, light/dark cycle was 12 hours per day, and a high-fat diet was induced for 10 weeks. An experiment was carried out while non-reducing end unsaturated mannuronic acid oligosaccharides (0.25 mg/kg) were intraperitoneally administered to experiment groups at an interval of 48 hours. 1-month and 17-month aged male C57BL/6J mice, as old mice, were purchased from Korea Basic Science Institute. The feeding environment was as follows: temperature was 20±2° C., relative humidity was 50±10%, light/dark cycle was 12 hours per day, and an experiment was carried out for 10 weeks. For experiment groups, non-reducing end unsaturated mannuronic acid oligosaccharides (0.2 mg/kg) were supplied to water. After the completion of the experiment, intestine contents of the experimental animals were collected, and 200 mg thereof were taken to secure pure DNA using Fast DNA™SPIN Kit for Soil kit on the basis of the method suggested in the kit. The concentration and purity of the extracted DNA were measured using a Nanodrop, and then the DNA concentration and purity were investigated on the basis of DNA band results extracted through agarose gel electrophoresis. For the amplification of bacterial 16S rRNA gene in isolated DNA, amplification PCR was performed using 27F forward primer (GAGTTTGATCMTGGCTCAG) containing V1-V3 hypervariable region and 518R reverse primer (WTTACCGCGGCTGCTGG) under conditions of initial denaturation at 94° C. for 5 min and 30 cycles of 30 seconds at 94° C., 45 seconds at 55° C., and 1 minute and 30 seconds at 72° C. PCR products purified through QIAquick gel extraction kit (Qiagen, Germany) were pyrosequenced using GS Junior Titanium system (Roche, Germany) as a DNA sequencer. Methods and reactions necessary for the pyrosequencing were carried out by ChunLab (Korea) according to the manufacturer's manuals.

Figure 7A:
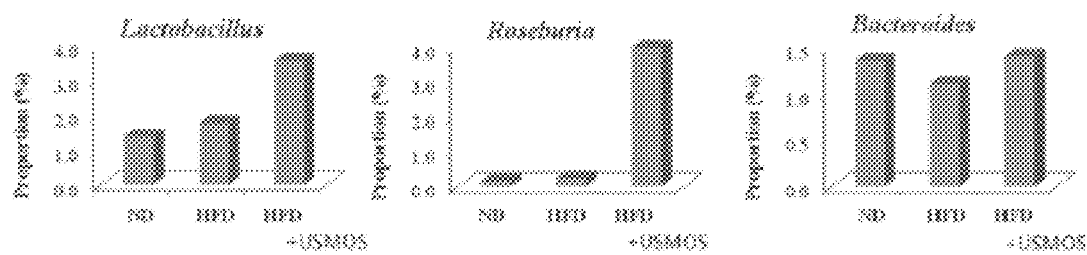
FIGS. 7*a* and 7*b* show intestinal microflora analysis results of obesity-induced rats by intraperitoneal administration of non-reducing end unsaturated mannuronic acid oligosaccharide (USMOS)
Figure 7B:
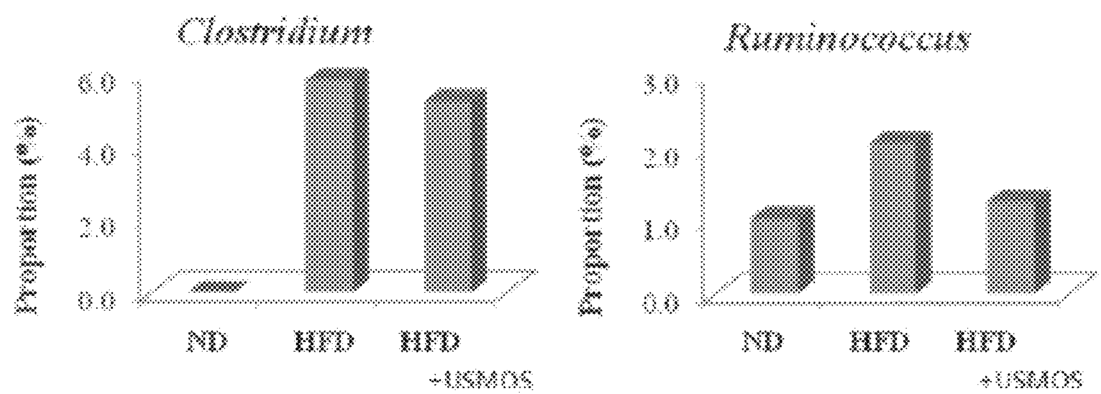

As shown in FIGS. 7*a* and 7*b*, in the intestinal microflora of obese rats receiving non-reducing end unsaturated mannuronic acid oligosaccharides, *Roseburia* sp. and *Lactobacillus* sp., which belong to gram positive bacteria (Firmicutes), were increased by about 4% and 2%, respectively, compared with the control (obesity-induced rats, high-fat diet (HFD)), resulting in the microflora change, and *Clostridium* sp. and *Ruminococcus* sp., which belong to gram negative bacteria (Bacteroidetes), were increased by about 1%, respectively.[4,5]

Figure 8:
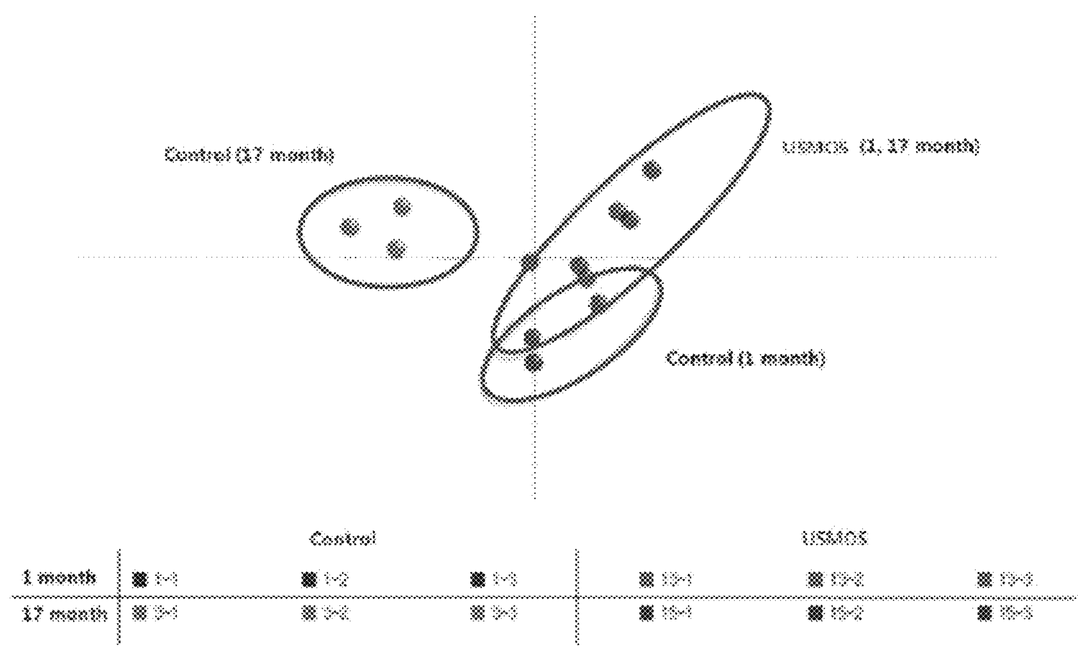
FIG. 8 shows principal coordinate (POC) analysis results of intestinal microflora of old mice by the uptake of a non-reducing end unsaturated mannuronic acid oligosaccharide (USMOS)

As shown in FIG. 8, it was verified through PCO analysis that, in the old mice drinking non-reducing end unsaturated mannuronic acid oligosaccharides, the intestinal microflora thereof was similar to that of 1-month aged mice, but were different from that of 17-month aged mice. In addition, it was verified that the above old mice formed similar intestinal microflora to 1-month aged mice taking non-reducing end unsaturated mannuronic acid oligosaccharides.

Figure 9:
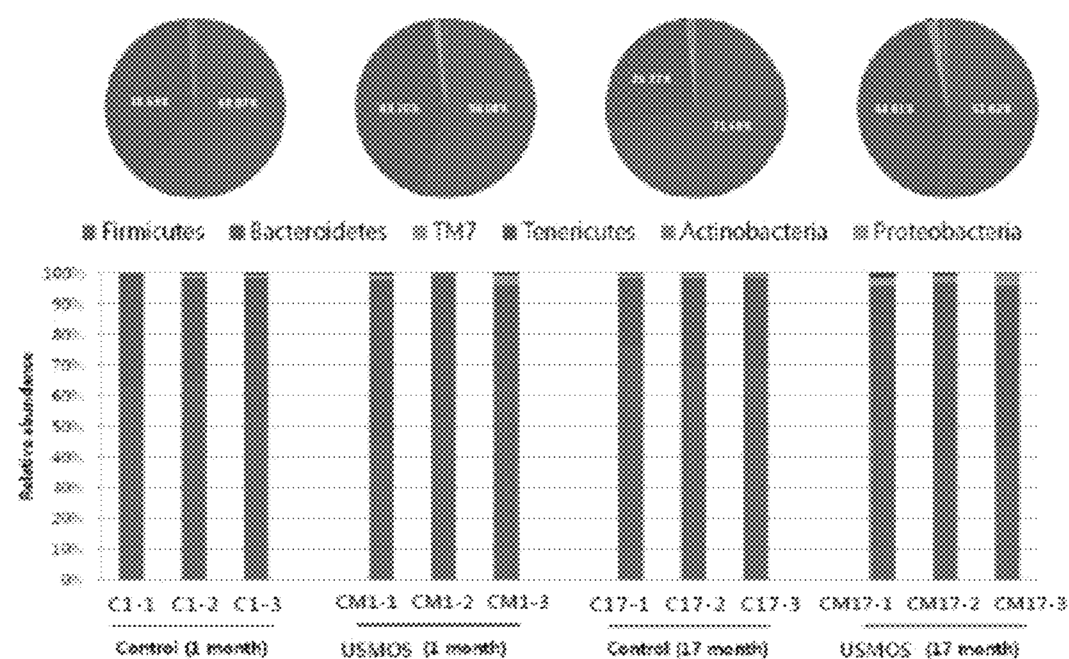
FIG. 9 shows phylum-level comparative analysis results of the intestinal microflora change of old mice by the uptake of non-reducing end unsaturated mannuronic acid oligosaccharide (USMOS)

As can be seen from FIG. 9, it was verified that, in the 17-month old mice taking non-reducing end unsaturated mannuronic acid oligosaccharides, gram positive bacteria (Bacteroidetes) were increased by about 22%, and relatively, gram negative bacteria (Firmicutes) were decreased by about 22%, compared with a control (17-month aged mice), and these results were similar to the intestinal microflora of the 1-month aged mice.

Example 6: Verification on Estrogen Sensitizer Function of Non-Reducing Unsaturated Mannuronic Acid Oligosaccharides 17β-estradiol used in the present study was purchased from Sigma (St. Louis, Mo., USA), and Dulbecco's modified Eagle's medium/F12 (DMEM/F12), fetal bovine serum, Opti-MEM medium, and penicillin-streptomycin were purchased from Gibco (NY, USA). PBS, cell count kit (CCK-8), RNeasy small kit, bovine insulin, and FuGENE HD were purchased from WeIGENE (Daegu, Korea), Dojindo Molecular Technologies (Tokyo, Japan), QIAGEN (Hiden, Germany), Cell Applications (San Diego, USA), and Promega (Madison, Wis., USA), respectively.

MCF-7 cells were cultured at 37° C. in DMEM/F12 medium supplemented with 10% bovine fetal serum, penicillin-streptomycine (100 U/ml), and 1% bovine insulin, and in order to measure estrogen sensitizer activity, the estrogen response element (ERE)-luciferase activity and the expression levels of pS2, PR, CTSD, PGC-1α, ERR, GATA3, and FOXO1 were investigated.

The cells were treated with non-reducing end unsaturated mannuronic acid oligosaccharides (0.1 mg/ml) for 48 hours, and then, in order to investigate ERE-luciferase activity, luciferase analysis was carried out by transfecting the MCF-7 cells with pEGFP-C1-ERα, 3×ERE TATA luc, and pRL-SV40 using FuGENE HD reagent, followed by dissolving. RNA extraction was carried out by GeneJET RNA purification kit method, and then the expression levels of pS2, PR, CTSD, PGC-1α, ERR, GATA3, and FOXO1 were investigated through real-time PCR.

Figure 10A:
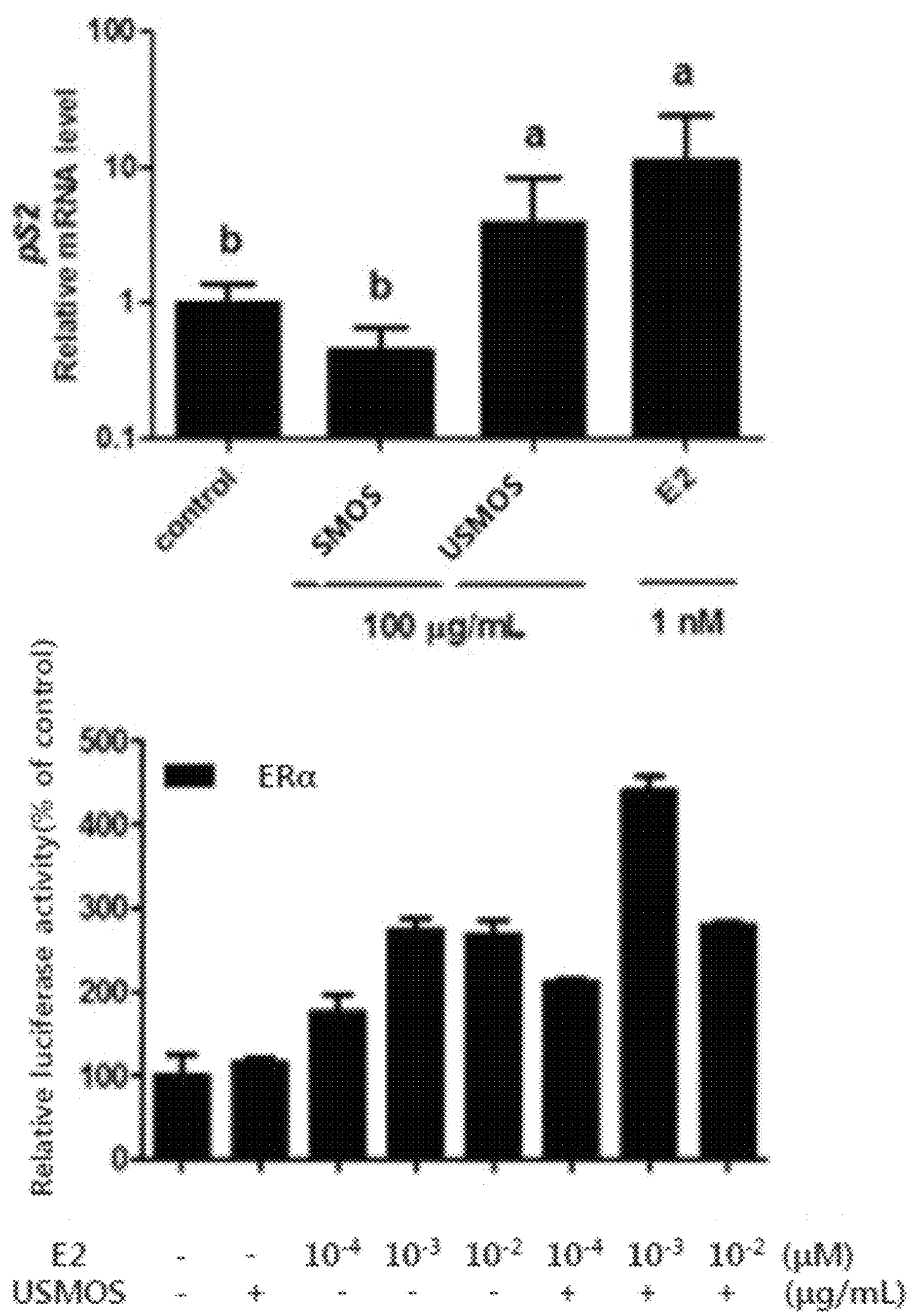
FIGS. 10*a* and 10*b* show mRNA expression levels of pS2, PR, and CTSD by the treatment with non-reducing end unsaturated mannuronic acid oligosaccharide (USMOS)
Figure 10B:
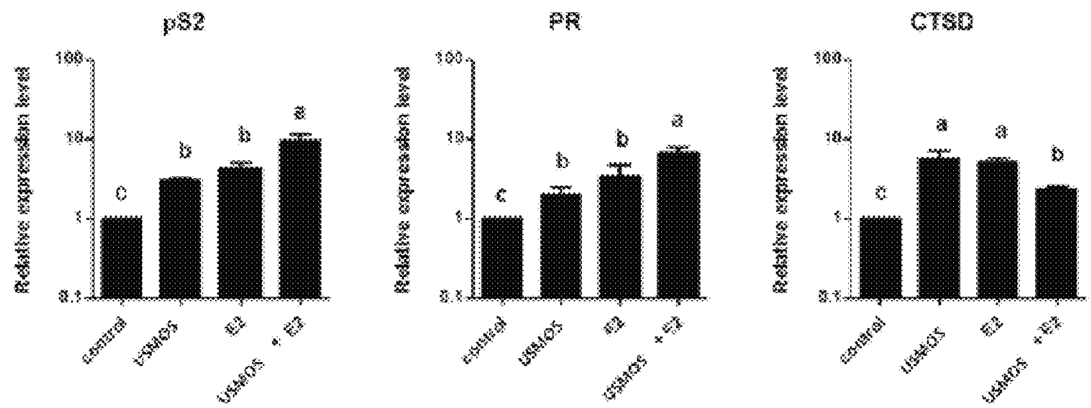

As shown in FIGS. 10*a* and 10*b*, it was verified that, unlike the non-reducing end saturated mannuronic acid oligosaccharides, the treatment with non-reducing end unsaturated mannuronic acid oligosaccharides increased the expression of pS2, which is an estrogen signal underlying gene, by about five times, compared with the control, and the co-treatment with estrogen (E2 and 17β-estradiol) and the non-reducing end unsaturated mannuronic acid oligosaccharides increased ERE luciferase activity and the expression of pS2 and PR, through estrogen receptor α (ERα), and reduced the expression of CTSD, and thus the non-reducing end unsaturated mannuronic acid oligosaccharides selectively regulated the expression of estrogen receptor α underlying signal genes.

Figure 11:
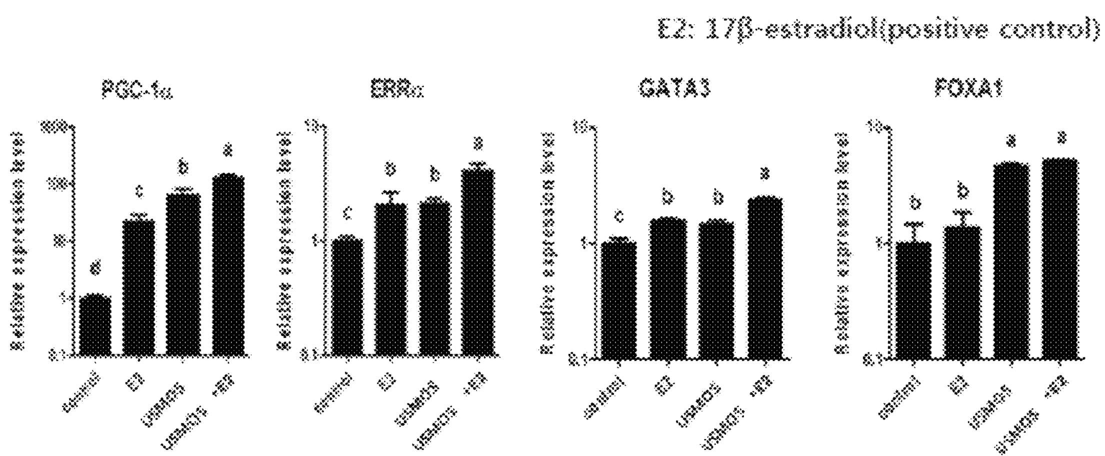
FIG. 11 shows mRNA expression levels of PGC-1α, ERRα, GATA3, and FOXA1 by the treatment with a non-reducing end unsaturated mannuronic acid oligosaccharide (USMOS)

As shown in FIG. 11, the treatment with non-reducing end unsaturated mannuronic acid oligosaccharides increased the expression of peroxisome proliferator-activated receptor c coactivator-1a (PGC-1α) and its transcription partner, estrogen related receptor α (ERRα), thereby increasing mRNA expression of GATA binding protein 3 (GATA3) and forkhead box protein A1 (FOXO1) together with ERα pathway, and thus the non-reducing end unsaturated mannuronic acid oligosaccharides had an estrogen sensitizer efficacy.

Example 7: Mechanism Diagram of Antiobesity, Anti-Diabetic, and Estrogen Sensitivity-Increasing Actions of Non-Reducing End Unsaturated Mannuronic Acid Oligosaccharides The overall diagram of mechanisms of antiobesity, anti-diabetic, and estrogen sensitivity-increasing actions of the non-reducing end unsaturated mannuronic acid oligosaccharides was presented in FIG. 12.

Figure 12:
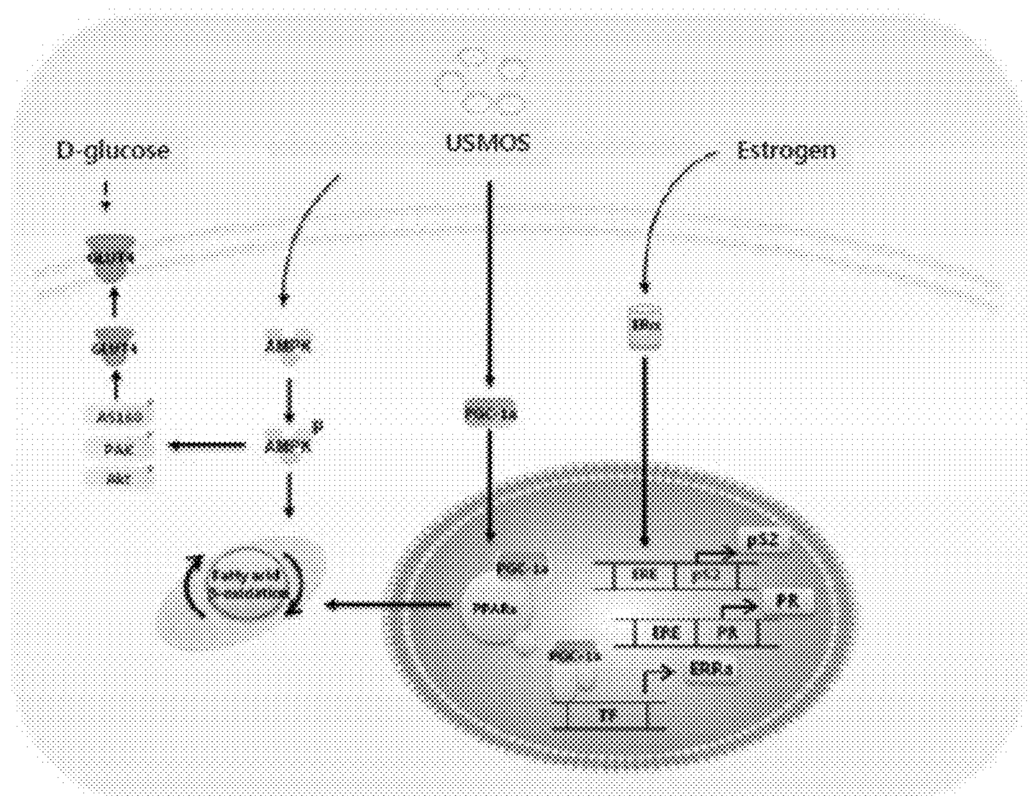
FIG. 12 shows a mechanism of non-reducing end unsaturated mannuronic acid oligosaccharide (USMOS)
Figure 13:
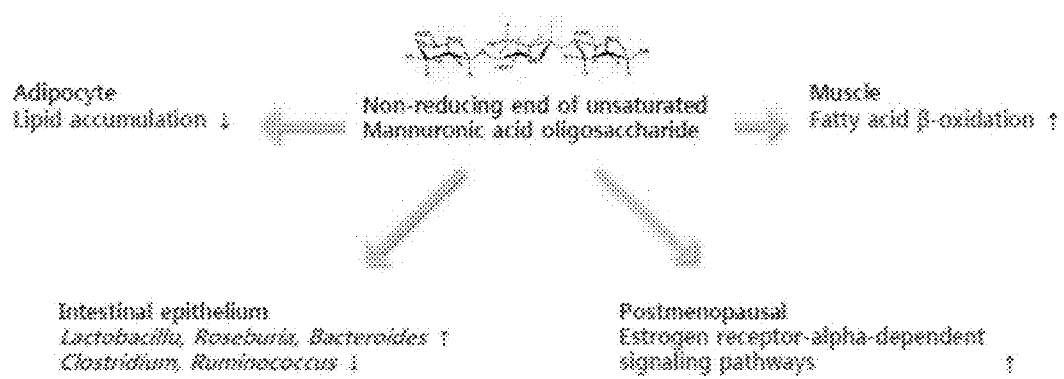
FIG. 13 shows various biological activity effects of non-reducing end unsaturated mannuronic acid oligosaccharide (USMOS).

As shown in FIG. 12, as a result of summarizing the mechanisms of antiobesity, anti-diabetic, and estrogen sensitivity-increasing actions by the treatment with non-reducing end unsaturated mannuronic acid oligosaccharides, it was verified that the treatment with non-reducing end unsaturated mannuronic acid oligosaccharides increased the expression of PGC-1α through AMPK activation, and activated estrogen-related receptor α, β, γ (ERRs), which are transcription partners of PGC-1α, thereby promoting fatty acid β oxidation, and thus the non-reducing end unsaturated mannuronic acid oligosaccharides had an antiobesity effect. In addition, as intramuscular AMPK has been reported to promote the fatty acid β oxidation metabolism, by mediating the fatty acid synthesis and degradation, and to increase the expression of mitochondria-related genes through PGC-1 expression, the non-reducing end unsaturated mannuronic acid oligosaccharides were anticipated to increase the expression and number of mitochondrial genes through AMPK activation and by increasing the expression of PCG-1α, and thus the non-reducing end unsaturated mannuronic acid oligosaccharides had an efficacy of improving insulin resistance.

It was verified that, the non-reducing end unsaturated mannuronic acid oligosaccharides, as an estrogen sensitizer, when used together with estrogen, increased the mRNA expression of GATA3 and FOXO1 through the estrogen receptor α (ERα) pathway, and increased the expression of ERRα and PGC-1α, and thus the non-reducing end unsaturated mannuronic acid oligosaccharide had an estrogen sensitizer function by activating ERE through the ERα pathway dependent on PGC-1α.

In addition, it was verified that the non-reducing end unsaturated mannuronic acid oligosaccharides improved the intestinal microflora in the body, and thus increased anti-obesity indicator strains (*Roseburia* sp. and *Lactobacillus* sp.) and decreased obesity indicator strains (*Clostridium* sp. and *Ruminococcus* sp.), and thus the non-reducing end unsaturated mannuronic acid oligosaccharides had antiobesity, anti-diabetic, intestinal microflora-improving, and estrogen sensitivity-increasing efficacies in combination.

REFERENCES

1. Qin J1 et al. A human gut microbial gene catalogue established by metagenomic sequencing. *nature.* 2010. 59-65

2. Human Microbiome Project Consortium. Structure, function and diversity of the healthy human microbiome. *nature.* 2012. 207-214

3. Turnbaugh P J et al. An obesity-associated gut microbiome with increased capacity for energy harvest. *nature.* 2006. 1027-31

4. Nadal I et al. ts in clostridia, bacteroides and immunoglobulin-coating fecal bacteria associated with weight loss in obese adolescents. *Int J Obes*(Lond). 2009. 758-767

5. Neyrinck A M et al. Prebiotic Effects of Wheat Arabinoxylan Related to the Increase in Bifidobacteria, Roseburia and Bacteroides/Prevotella in Diet-Induced Obese Mice. *PLoS One.* 2011. e20944

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

What is claimed is:

1. A pharmaceutical composition comprising a non-reducing end unsaturated alginate oligosaccharide having a molecular weight of 100-3,000 Da, and 17β-estradiol, wherein the alginate oligosaccharide is obtained by lysing polymannuronate as a substrate with alginate lyase.

2. The composition of claim 1, wherein the non-reducing end unsaturated alginate oligosaccharide comprises one to ten mannuronic acids or guluronic acids.

3. The composition of claim 1, wherein the ratio of mannuronic acid:guluronic acid is 1.2-5.0:1.

* * * * *